(12) United States Patent
Thorgilsdottir et al.

(10) Patent No.: US 8,858,481 B2
(45) Date of Patent: Oct. 14, 2014

(54) CERVICAL COLLAR WITH REDUCED VASCULAR OBSTRUCTION

(75) Inventors: Thora Thorgilsdottir, Reykjavik (IS); Arni Thor Ingimundarson, Ladera Ranch, CA (US); Palmi Einarsson, San Juan Capistrano, CA (US)

(73) Assignee: Ossur HF, Reykjavik (IS)

(*) Notice: Subject to any disclaimer, the term of this patent is extended or adjusted under 35 U.S.C. 154(b) by 117 days.

(21) Appl. No.: 13/456,601

(22) Filed: Apr. 26, 2012

(65) Prior Publication Data

US 2012/0209160 A1 Aug. 16, 2012

Related U.S. Application Data

(63) Continuation of application No. 12/729,536, filed on Mar. 23, 2010, now Pat. No. 8,679,044, which is a continuation-in-part of application No. 12/629,197, filed on Dec. 2, 2009, now Pat. No. 7,981,068.

(60) Provisional application No. 61/241,528, filed on Sep. 11, 2009, provisional application No. 61/119,425, filed on Dec. 3, 2008.

(51) Int. Cl.
 *A61F 5/00* (2006.01)
(52) U.S. Cl.
 USPC ........................................ 602/18; 128/DIG. 23
(58) Field of Classification Search
 USPC .......................... 602/17–19, 32; 128/DIG. 23
 See application file for complete search history.

(56) References Cited

U.S. PATENT DOCUMENTS

| | | | |
|---|---|---|---|
| 2,801,630 | A | 8/1957 | Moore |
| 2,818,063 | A | 12/1957 | Smith et al. |
| 2,820,455 | A | 1/1958 | Hall |
| 2,911,970 | A | 11/1959 | Bartels et al. |
| 3,024,784 | A | 3/1962 | Monfardini |
| 3,042,027 | A | 7/1962 | Monfardini |
| 3,285,243 | A | 11/1966 | Yellin |
| 3,285,244 | A | 11/1966 | Cottrell |

(Continued)

FOREIGN PATENT DOCUMENTS

| | | |
|---|---|---|
| DE | 10057286 A1 | 5/2002 |
| FR | 2814362 A1 | 3/2002 |

(Continued)

OTHER PUBLICATIONS

Chinese Search Report from corresponding CN Application Serial No. 200980147713.8, Dec. 6, 2012.

(Continued)

*Primary Examiner* — Michael A. Brown
(74) *Attorney, Agent, or Firm* — Workman Nydegger

(57) ABSTRACT

A cervical collar has an anterior portion and a posterior portion having side extending portions removably connecting to the anterior portion. The posterior portion includes a rigid or semi-rigid main support piece and a resilient edge integrally secured to at least a substantial portion of a periphery of the main support piece that is substantially more flexible than the main support piece. The main support piece defines opposed upper side sections and a lower section. The upper side sections extend upwardly from the side extending portions and are oriented toward a proximal middle region and spaced apart by a first distance. The lower section extends continuously between the side extending portions and is spaced a second distance from the upper side sections.

13 Claims, 8 Drawing Sheets

(56) References Cited

U.S. PATENT DOCUMENTS

| | | |
|---|---|---|
| 3,306,284 A | 2/1967 | McKinley |
| 3,320,950 A | 5/1967 | McElvenny |
| 3,504,667 A | 4/1970 | McFarlane |
| 3,512,523 A | 5/1970 | Barnett |
| 3,756,226 A | 9/1973 | Calabrese et al. |
| 3,916,885 A | 11/1975 | Gaylord, Jr. |
| 4,173,973 A | 11/1979 | Hendricks |
| 4,205,667 A | 6/1980 | Gaylord, Jr. |
| 4,325,363 A | 4/1982 | Berkeley |
| 4,401,111 A | 8/1983 | Blackstone |
| 4,413,619 A | 11/1983 | Garth |
| 4,520,801 A * | 6/1985 | Lerman ............................. 602/18 |
| 4,538,597 A | 9/1985 | Lerman |
| 4,562,833 A | 1/1986 | Pujals, Jr. |
| 4,677,969 A | 7/1987 | Calabrese |
| 4,708,129 A | 11/1987 | Pujals, Jr. |
| 4,712,540 A | 12/1987 | Tucker et al. |
| 4,745,922 A | 5/1988 | Taylor |
| 4,854,306 A | 8/1989 | Pujals, Jr. |
| 4,886,052 A | 12/1989 | Calabrese |
| 4,940,043 A | 7/1990 | Burns et al. |
| 4,987,891 A | 1/1991 | Gaylord et al. |
| 5,005,563 A | 4/1991 | Veale |
| 5,038,759 A | 8/1991 | Morgenstern |
| 5,058,572 A | 10/1991 | Schmid et al. |
| 5,060,637 A | 10/1991 | Schmid et al. |
| 5,097,824 A * | 3/1992 | Garth ............................. 602/18 |
| 5,156,588 A | 10/1992 | Marcune et al. |
| 5,180,361 A | 1/1993 | Moore et al. |
| 5,215,517 A | 6/1993 | Stevenson et al. |
| 5,230,698 A | 7/1993 | Garth |
| 5,275,581 A | 1/1994 | Bender |
| 5,302,170 A | 4/1994 | Tweardy |
| RE34,714 E | 8/1994 | Burns et al. |
| 5,346,461 A | 9/1994 | Heinz et al. |
| 5,366,438 A | 11/1994 | Martin, Sr. |
| 5,385,535 A | 1/1995 | McGuinness |
| 5,433,696 A | 7/1995 | Osti |
| 5,437,612 A | 8/1995 | Moore et al. |
| 5,437,617 A | 8/1995 | Heinz et al. |
| 5,445,602 A | 8/1995 | Grim et al. |
| D368,527 S | 4/1996 | Brooke |
| D369,660 S | 5/1996 | Myoga |
| 5,520,619 A | 5/1996 | Martin |
| RE35,290 E | 7/1996 | Druskoczi |
| 5,588,957 A | 12/1996 | Martin, Sr. |
| 5,593,382 A | 1/1997 | Rudy, Jr. et al. |
| 5,622,529 A | 4/1997 | Calabrese |
| 5,624,387 A | 4/1997 | McGuinness |
| D379,232 S | 5/1997 | Brooke |
| 5,632,722 A | 5/1997 | Tweardy et al. |
| 5,688,229 A * | 11/1997 | Bauer ............................. 602/18 |
| 5,716,335 A | 2/1998 | Iglesias et al. |
| 5,728,054 A | 3/1998 | Martin |
| D393,718 S | 4/1998 | Traut et al. |
| 5,785,670 A | 7/1998 | Hiebert |
| 5,788,658 A | 8/1998 | Islava |
| 5,795,315 A | 8/1998 | Traut et al. |
| 5,797,713 A | 8/1998 | Tweardy et al. |
| 5,797,863 A | 8/1998 | Kohnke |
| RE35,940 E | 10/1998 | Heinz et al. |
| 5,865,773 A | 2/1999 | Koledin |
| 5,904,662 A | 5/1999 | Myoga |
| 5,934,599 A | 8/1999 | Hammerslag |
| 5,964,722 A | 10/1999 | Goralnik et al. |
| 5,976,098 A | 11/1999 | Sereboff |
| 5,993,403 A | 11/1999 | Martin |
| 6,027,467 A | 2/2000 | Nakamura et al. |
| 6,036,664 A | 3/2000 | Martin, Sr. et al. |
| D422,710 S | 4/2000 | Maynard |
| 6,045,523 A | 4/2000 | Donaldson |
| 6,050,965 A | 4/2000 | Pillai |
| 6,056,711 A | 5/2000 | Donamski et al. |
| 6,058,517 A | 5/2000 | Hartunian |
| RE36,745 E | 6/2000 | Rudy, Jr. et al. |
| 6,071,255 A | 6/2000 | Calabrese |
| 6,071,256 A | 6/2000 | Lam |
| 6,090,058 A | 7/2000 | Traut et al. |
| 6,165,146 A | 12/2000 | Giebeler |
| 6,183,501 B1 | 2/2001 | Latham |
| 6,202,953 B1 | 3/2001 | Hammerslag |
| 6,245,033 B1 | 6/2001 | Martin |
| 6,254,560 B1 | 7/2001 | Tweardy et al. |
| 6,308,345 B1 | 10/2001 | Williams, Jr. |
| 6,423,020 B1 | 7/2002 | Koledin |
| 6,458,090 B1 | 10/2002 | Walpin |
| 6,494,854 B1 | 12/2002 | Visness et al. |
| D475,139 S | 5/2003 | Myoga |
| 6,663,581 B1 | 12/2003 | Calabrese |
| 6,663,630 B2 | 12/2003 | Farley et al. |
| 6,726,643 B1 | 4/2004 | Martin |
| 6,740,055 B2 | 5/2004 | Dominguez |
| 6,770,046 B2 | 8/2004 | Hansen |
| 6,872,188 B2 | 3/2005 | Caille et al. |
| 6,913,584 B2 | 7/2005 | Rudy, Jr. et al. |
| 6,921,376 B2 | 7/2005 | Tweardy et al. |
| 6,926,686 B2 | 8/2005 | Cheatham |
| 7,018,351 B1 | 3/2006 | Iglesias et al. |
| 7,041,073 B1 | 5/2006 | Patron |
| 7,070,573 B2 | 7/2006 | Axelsson |
| 7,090,652 B2 | 8/2006 | Santelli, Jr. |
| 7,090,653 B2 | 8/2006 | Moeller |
| 7,128,724 B2 | 10/2006 | Marsh |
| 7,141,031 B2 | 11/2006 | Garth et al. |
| 7,198,610 B2 | 4/2007 | Ingimundarson et al. |
| D542,919 S | 5/2007 | Leatt |
| 7,258,677 B2 | 8/2007 | Rudy, Jr. et al. |
| 7,291,121 B2 | 11/2007 | Rudy, Jr. et al. |
| 7,297,127 B2 | 11/2007 | Lee et al. |
| 7,311,686 B1 | 12/2007 | Iglesias et al. |
| 7,371,221 B1 | 5/2008 | Baker |
| 7,371,222 B2 | 5/2008 | Heinz et al. |
| 7,399,288 B2 | 7/2008 | Chao |
| D616,555 S | 5/2010 | Thorgilsdottir et al. |
| D616,996 S | 6/2010 | Thorgilsdottir et al. |
| D616,997 S | 6/2010 | Thorgilsdottir et al. |
| 7,815,585 B2 | 10/2010 | Vollbrecht |
| 7,896,827 B2 | 3/2011 | Ingimundarson et al. |
| 7,981,068 B2 | 7/2011 | Thorgilsdottir et al. |
| 8,038,636 B2 | 10/2011 | Thorgilsdottir et al. |
| 2002/0138028 A1 | 9/2002 | Rudy, Jr. et al. |
| 2002/0156408 A1 | 10/2002 | Cheatham |
| 2002/0156409 A1 | 10/2002 | Lee et al. |
| 2002/0169401 A1 | 11/2002 | Walpin |
| 2002/0173737 A1 | 11/2002 | Miyaji et al. |
| 2003/0055367 A1 | 3/2003 | Dominguez |
| 2003/0060744 A1 * | 3/2003 | Caille et al. .................... 602/18 |
| 2003/0181838 A1 | 9/2003 | Garth |
| 2004/0039318 A1 | 2/2004 | Santelli, Jr. |
| 2005/0101896 A1 | 5/2005 | Calabrese |
| 2007/0027418 A1 | 2/2007 | Calco et al. |
| 2007/0073203 A1 | 3/2007 | Moenning et al. |
| 2007/0270728 A1 | 11/2007 | Chao |
| 2009/0247918 A1 | 10/2009 | Patron |
| 2010/0137768 A1 | 6/2010 | Thorgilsdottir et al. |
| 2010/0268139 A1 | 10/2010 | Garth |
| 2011/0066094 A1 | 3/2011 | Thorgilsdottir et al. |

FOREIGN PATENT DOCUMENTS

| | | |
|---|---|---|
| GB | 2165157 A | 4/1986 |
| GB | 2453996 A | 4/2009 |
| JP | 2007330808 A | 12/2007 |
| WO | 95/22304 A1 | 8/1995 |
| WO | 96/40018 A1 | 12/1996 |
| WO | 9409728 A1 | 5/1997 |

OTHER PUBLICATIONS

European Search Report from corresponding EP Application Serial No. 13165274.5, Jul. 17, 2013.

International Search Report from corresponding PCT Application No. PCT/US2013/041586, Oct. 1, 2013.

(56) References Cited

OTHER PUBLICATIONS

Levangie et al., "Joint Structure and Function: A Comprehensive Analysis", Fourth Edition,Chapter 4: The Vertebral Column, 2005 F.A. Davis Company, Philadelphia, PA, pp. 161-164.
Hsu et al., AAOS Atlas of Orthoses and Assistive Devices, Mosby, Elsevier Fourth Edition, 2008, Philadelphia, PA, p. 117-122.
International Search Report from PCT Application No. PCT/US2009/006335, Mar. 11, 2010, 3 Pages.
Written Opinion of the International Searching Authority from PCT Application No. PCT/US2009/006335, Mar. 11, 2010, 5 pages.
Philadelphia Tracheotomy Collar, Product Information Sheet, obtained from www.ossur.com, prior to Aug. 6, 2010, 1 page.
Product Information Sheet, Platazote Sheets, WBC Industries, obtained from www.wbcindustries.com prior to Aug. 6, 2010, 2 pages.
International Search Report and Written Opinion from PCT Application No. PCT/US2010/002199, Dec. 27, 2010, 9 pages.
International Search Report issued in PCT/US2009/006335, Mar. 11, 2010, 3 pages.
Written Opinion of the International Searching Authority issued in PCT/US2009/006335, Mar. 11, 2010, 5 pages.

* cited by examiner

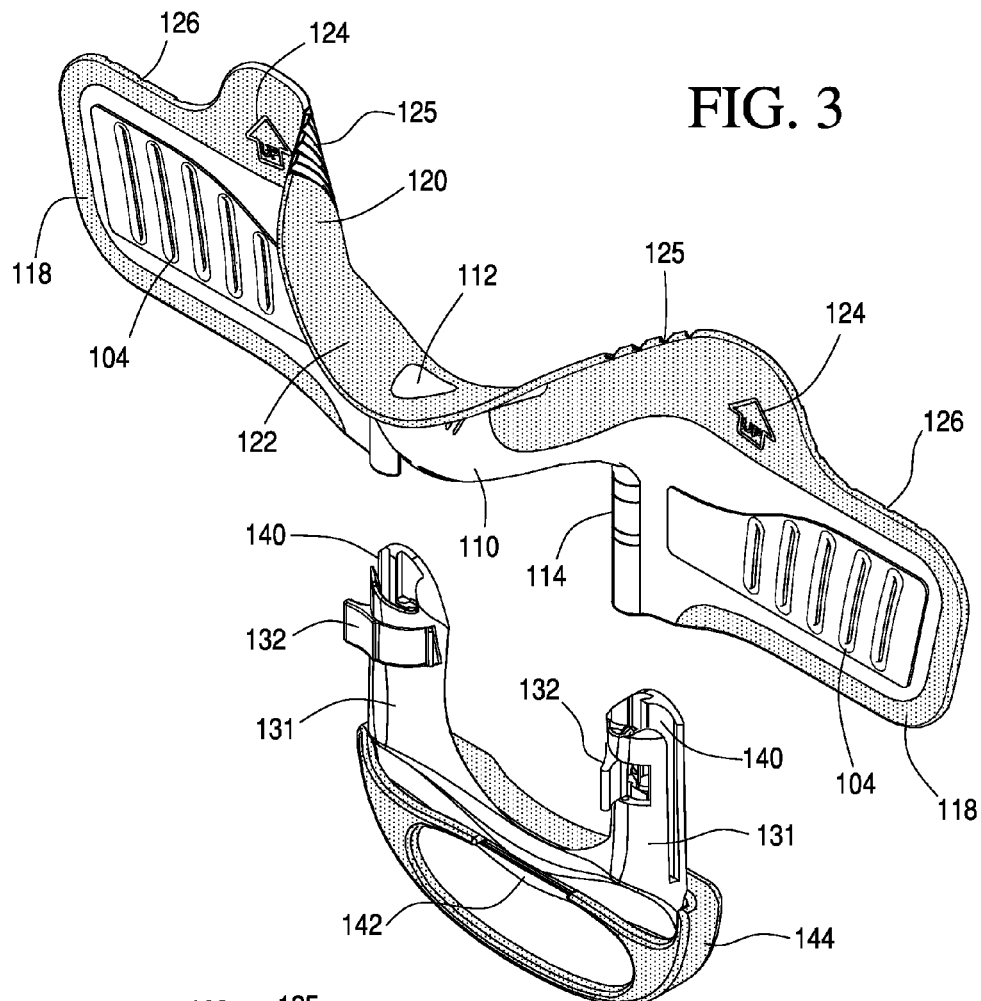
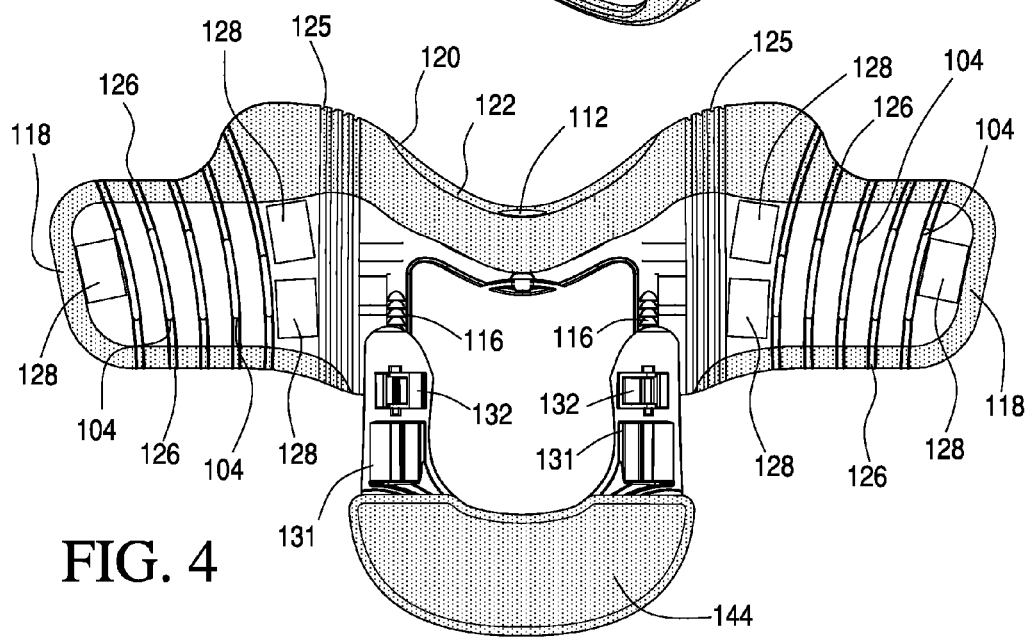

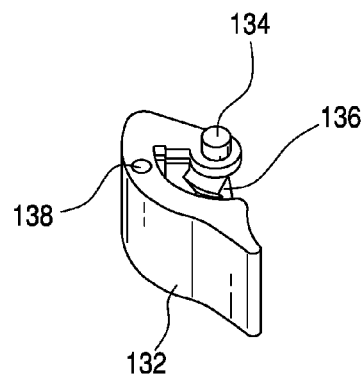
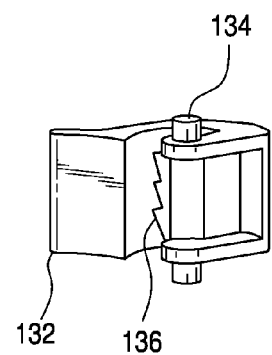
FIG. 5　　　　　FIG. 6
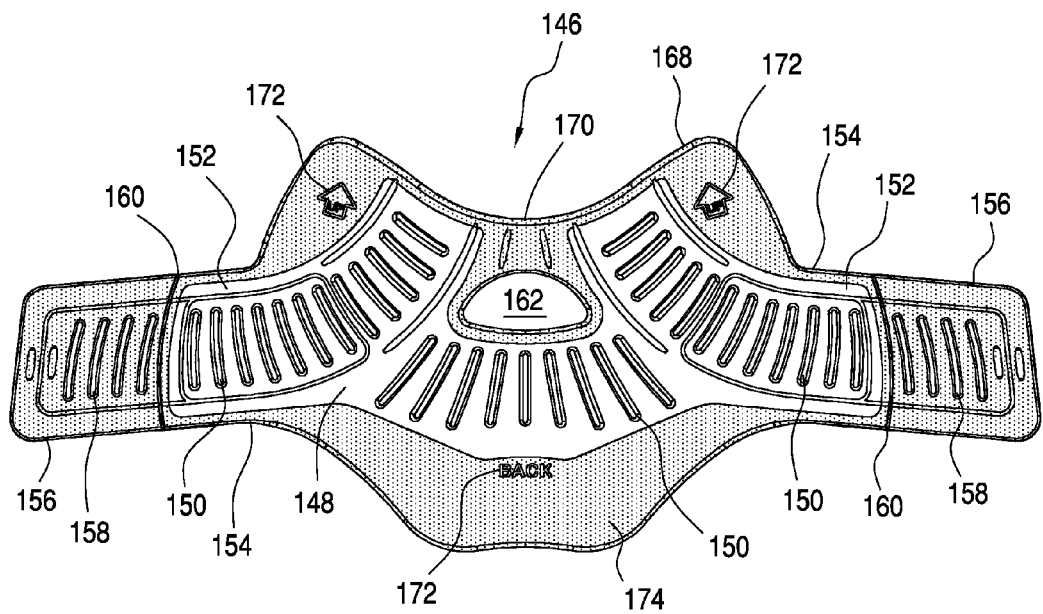
FIG. 7

CERVICAL COLLAR WITH REDUCED VASCULAR OBSTRUCTION

This application is a continuation of prior application Ser. No. 12/729,536, filed Mar. 23, 2010, which is a continuation-in-part of prior application Ser. No. 12/629,197, filed Dec. 2, 2009, now U.S. Pat. No. 7,981,068, granted Jul. 19, 2011, which application claims the benefit of U.S. Provisional Application No. 61/119,425, filed Dec. 3, 2008, and U.S. Provisional Application No. 61/241,528, filed Sep. 11, 2009, which applications are hereby incorporated by reference herein in their entirety, inclusive of their specifications, claims, and drawings.

FIELD OF THE INVENTION

The invention relates generally to the field of orthopedic or prosthetic devices and more specifically to cervical collars having reduced vascular obstruction.

BACKGROUND

Cervical collars are used in the treatment, stabilization, immobilization, and therapy of cervical trauma. Since cervical spinal injuries are often accompanied by severe head trauma, the first response is often to immobilize the neck (columna cervicalis; cervical vertebral/spinal column). For example, some collars are intended to provide support for whiplash and other such injuries where support for the head and neck is needed. Other collars are intended for near complete immobilization of the head and neck, such as in an EMS (Emergency Medical Services) pre-hospital setting. The immobilization is done to prevent further damage in waiting for subsequent surgical operation or treatment; sometimes, however, the immobilization is used as a final treatment of spinal injuries.

In such an EMS pre-hospital setting, which typically involves vehicular accident victims or others who have suffered head trauma, victims are also at a substantial risk of having a cervical spine injury ("Effect of cervical hard collar on intracranial pressure after head injury," *ANZ J Surg* 2002 June; 56(6):511-3; Mobbs et al.). In such cases, a rigid cervical collar can be applied until it is determined that there is no underlying cervical spine injury (id.).

Thus, it is recognized that spinal immobilization can be achieved by the application of a rigid collar to protect the neck and forms an integral part of care of the injured. However, patients with combined head and neck injuries often have higher intracranial pressure (ICP) that may be caused by intracranial hemorrhage and or contusion of the brain.

Intracranial pressure is a dangerous condition, and a number of studies have shown that the use of rigid cervical collars can actually raise intracranial pressure. In particular, the very nature of rigid cervical collar designs predisposes to vascular obstruction of blood draining from the brain, which theoretically may lead to an increase in intracranial pressure.

In fact, some current types of rigid cervical collars are known to provide an increase in pressure on neck veins (vena jugularis externa and interna; external and internal jugular veins) thereby causing stasis in the veins and leading to an increase intracranial pressure. An increase in intracranial pressure deceases cerebral perfusion and exacerbates ischemia, and thus can lead to an increase in the chances for a secondary brain injury can occur ("The effect of rigid cervical collars on internal jugular vein dimensions," *Acad Emerg Med;* January 2010, Vol. 17, No. 100-102; Stone et al.).

This suggests that in patients having head injuries, when a rigid collar is used to stabilize the cervical spinal column, the rigid collar should be removed as soon as cervical spine injury has been ruled out.

There is an apparent need then for a short and long term use cervical collar that does not obstruct the blood drain from the brain.

SUMMARY

An embodiment of a cervical collar according to the present disclosure provides sufficient stabilization and immobilization of the cervical spinal column, while at the same time having reduced vascular obstruction. In particular, an embodiment of a cervical collar according to the present disclosure has less contact with, and produces less pressure on, the sternocleidomasteoidus (sternomastoid muscle) area of the neck and is thus less likely to cause pressure on the veins in the neck. This may decrease the possibility of vascular obstruction of blood draining from the brain and thus, the cervical collar according to the present disclosure is less likely to increase intracranial pressure.

Specifically, the shape of the cervical collar at the anterior portion, when applied to the neck of a patient, defines a clearance of the neck veins by way of fold lines formed along the anterior portion of the collar. In an exemplary embodiment, the fold lines can be formed by utilizing a living-hinge structure for each fold line.

The fold lines are provided along a posterior surface of the anterior cervical collar portion. The fold lines are generally arranged perpendicularly on either side of an open access area defined along the anterior cervical collar portion. The fold lines allow the generally rigid plastic of the cervical collar to naturally curve into a shape that provides the appropriate clearance for the neck veins.

The central portion of the anterior portion of the cervical collar attaches to the sternal extension adjustment part, and is relatively flat, while the curve of the anterior portion of the cervical collar provided by the fold lines forms a generally rounded corner leaving a gap opposite to the relatively curved surface of the neck at the location of the large cervical veins (vena jugularis externa and interna; external and internal jugular veins) draining blood from the brain, thus, providing reduced vascular obstruction, and reducing the likelihood of an increase in intracranial pressure.

The fold lines providing the reduced vascular obstruction for the cervical collar can be implemented in a cervical collar having height and circumferential adjustment, in order to accommodate a wide variety of sizes of different patients and to accommodate size changes caused by increased or decreased swelling of the affected anatomical portions of the patients. However, the fold lines can be provided to any cervical collar configuration, adjustable in size or not.

Additional features of the cervical collar can include a removable sternal adjustable height support piece to allow the collar to be adjusted or removed, for example for cleaning or to check for pressure sores, without removing life support attachments such as breathing and feeding tubes.

Flexible or compliant edges and anatomically shaped portions on the cervical collar can be provided to accommodate different sized users, to accommodate changes in anatomical shape due to an increase or decrease in swelling, and to prevent pressure peaks, even if the collar is improperly applied to the patient.

The disclosed cervical collar is configured to conform to the anatomy of the patient, and to be a generally constant contact collar that contacts the skin of the patient. With this in mind, the collar allows some amount of patient movement, permitting the collar to move with the patient while still providing clearance with, and producing less pressure on, the sternomastoid muscle area of the neck. This arrangement makes it less likely that the collar provides pressure on the veins along the neck.

The combination of flexible or compliant edges and anatomically shaped portions on the cervical collar along with ventilation mechanisms, such as ventilation slots, allow the collar to have intimate contact with the skin of the patient (with or without the use of a liner).

In a variation of the aforementioned embodiments, a foam cervical collar includes recessed or cutout surfaces that provide a gap between the cervical collar and the neck, thus providing clearance with, and producing less pressure on, the sternomastoid muscle area of the neck making the collar less likely to form pressure on the veins along the neck.

BRIEF DESCRIPTION OF THE DRAWINGS

These and other features, aspects, and advantages of the present invention will become better understood with regard to the following description, appended claims, and accompanying drawings where:

FIG. 3 is a perspective view of the anterior portion of the cervical collar shown in FIG. 1 with the height adjustment piece separated therefrom for the sake of clarity;

FIG. 4 is a rear view of the anterior portion of the cervical collar shown in FIG. 1;

FIGS. 5 and 6 are respectively a side perspective and rear perspective view of the locking button of the height adjustment piece of the cervical collar shown in FIG. 1;

FIG. 7 is a front view of a posterior portion of a cervical collar in accordance with the present disclosure;

Figure 1:
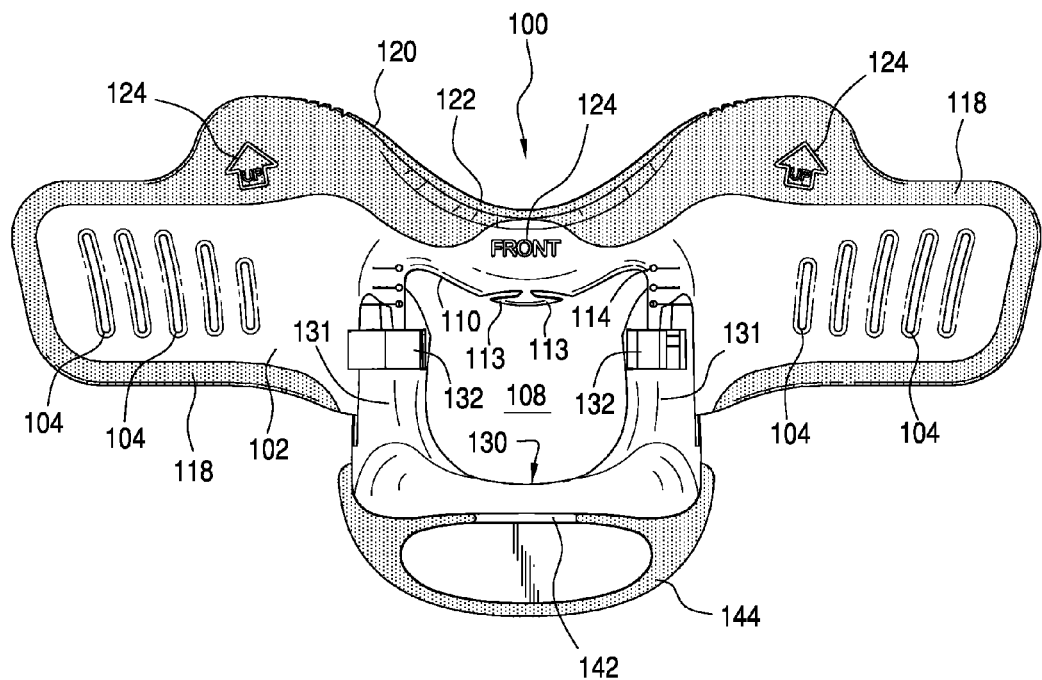
FIG. 1 is a front view of an anterior portion of a cervical collar in accordance with the present disclosure.
Figure 2:
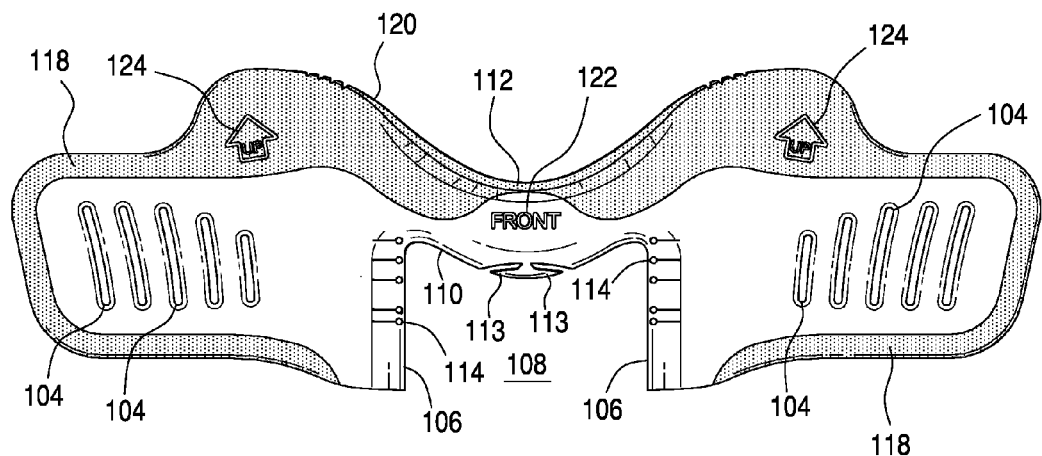
FIG. 2 is a front view of the anterior portion of the cervical collar shown in FIG. 1 with the height adjustment piece removed for the sake of clarity.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of a cervical collar having reduced vascular obstruction and the components thereof, and in no way limit the structures or configurations of a cervical collar having reduced vascular obstruction and components thereof according to the present disclosure.

DETAILED DESCRIPTION

A. Environment and Context

Embodiments of an orthopedic device are provided for use in stabilizing and supporting anatomical portions of a patient, for example, the neck and head of a patient.

Although the embodiments of the disclosure are adapted for supporting and stabilizing anatomical portions of a large number of patients having various anatomical shapes and sizes, the embodiments of the disclosure may also be dimensioned to accommodate different types, shapes and sizes of anatomical portions.

Exemplary materials and configurations for components of the orthopedic device, such as the structural supports or shells and flexible or compliant portions, as well as exemplary uses and connection mechanisms are described in detail in U.S. Pat. Nos. 5,180,361, granted January 1993, U.S. Pat. No. 5,445,602, granted August 1995, U.S. Pat. No. 5,622,529, granted April 1997, U.S. Pat. No. 5,632,722, granted May 1997, U.S. Pat. No. 5,716,335, granted February 1998, U.S. Pat. No. 6,071,255, granted June 2000, U.S. Pat. No. 6,254,560, granted July 2001, U.S. Pat. No. 6,663,581, granted December 2003, U.S. Pat. No. 7,018,351, granted March 2006, and U.S. Pat. No. 7,198,610, granted April 2007, and all incorporated herein in the entirety by reference.

For ease of understanding the disclosed embodiments of an orthopedic device, the anterior and posterior portions of the orthopedic device are described independently. It will be recognized that the anterior and posterior portions of the orthopedic device function together to form a supporting and stabilizing collar that encompasses the anatomical portions of the wearer.

For further ease of understanding the embodiments of an orthopedic device as disclosed herein, a description of a few terms is necessary. As used herein, the term "proximal" has its ordinary meaning and refers to a location situated next to or near the point of attachment or origin or a central point, or located toward the center of the body. Likewise, the term "distal" has its ordinary meaning and refers to a location that is situated away from the point of attachment or origin or a central point, or located away from the center of the body. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," "compliant," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "compliant" is used to qualify such flexible features as generally conforming to the shape of another object when placed in contact therewith, via any suitable natural or applied forces, such as gravitational forces, or forces applied by external mechanisms, for example, strap mechanisms. The term "resilient" is used to qualify such flexible features as generally returning to an initial general shape without permanent deformation. As for the term "semi-rigid," this term is used to connote properties of support members or shells that provide support and are free-standing, however such support members or shells may have some degree of flexibility or resiliency.

B. Detailed Description of an Anterior Portion of an Orthopedic Device

An anterior portion 100 of an orthopedic device, such as a cervical collar, is shown in FIGS. 1-4. The anterior portion 100 generally includes three components.

The first component is a main support piece 102. The main support piece 102 has the form of a rigid or semi-rigid shell that is formed slightly out of plane to extend towards first and second sides. The main support piece 102 includes a plurality of spaced substantially vertically oriented or angled arcuate slots 104 that aid with ventilation of the orthopedic device in use, and also provide additional resiliency to allow the main support piece 102 to be bent to conform to the anatomical portion of the user, such as the neck.

The main support piece 102 also includes two spaced depending projections 106 that define an open access area 108 therebetween to allow access to, for example, the trachea of a wearer.

A thickened support section 110 runs along the main support piece 102 from a first end of a first depending projection 106 in a generally U-shape along the main support piece 102 to a first end of a second depending projection 106. The thickened support section 110 provides additional support for the main support piece 102 and for the adjustable height support 130 discussed in detail below. As an alternative, a rod or stay that is flexible, such as an aluminum rod, can be integrated into the main support piece 102 in place of the thickened support section 110.

In addition to the thickened support section 110, a supporting spring portion 112 is formed, for example, to support the chin of patient. The supporting spring portion 112 provides a stable but dampening support under the chin of the patient, and restricts flexion. The use of the supporting spring portion 112 in combination with a flexible edge (discussed in more detail below) also aids with reducing or eliminating pressure points.

Ribs 113 are formed below the spring 112 to provide connection points for an attachment piece (chin strut) used to connect a chest plate (forming part of a thoracic extension) to the cervical collar. An exemplary thoracic extension is described in detail in U.S. Pat. No. 6,921,376, granted Jul. 26, 2005, and herein incorporated in the entirety by reference.

Height adjustment indicia 114 are provided on the depending projections to provide easy sizing of the cervical collar using predetermined sizes, such as small, medium, large, etc. The height adjustment indicia 114 can be in the form of standardized, color coded markings and/or lines that reflect standardized marking systems used to indicate patient sizes. Other indicia, such as alphanumeric labels, can also be used. The height adjustment indicia 114 cooperate with leading edges of the adjustable height support 130 to provide an indication of the current sizing of the cervical collar.

As seen in FIG. 4, a plurality of locking projections, or ratchets, 116 are formed along each of the depending projections 106 in a linear fashion to cooperate with the adjustable height support 130 discussed in detail below. The locking projections 116 can have a rounded first edge having a first thickness that tapers out to a linear edged having a second thickness that is larger than the first thickness, wherein the linear edge is configured to engage with associated teeth 136 positioned on the adjustable height support 130, as discussed below.

As also shown in FIG. 4, the posterior side of the main support piece 102 includes liner connection points 128, where a suitable removable liner, such as a disposable hydrophilic foam pad liner, can be connected to the cervical collar. The connection points 128 can be formed as hook members, integrally formed on the main support piece 102, for example, by injection molding, and configured to cooperate with loops formed on the liner or attached to the liner. Alternative connection mechanisms, such as hook and loop fasteners applied by adhesive or snap fasteners, can also be used. The use of the integrally formed hooks for the connection points 128 eliminates sharp or rough edges associated with the use of plastic rivets to connect a liner to an orthopedic device, thus providing a more comfortable fit with a reduced chance of pressure sores developing.

The main support piece 102 includes resilient or flexible edges 118 formed along the periphery of the main support piece 102, for example, by overmolding a resilient or compliant material thereon. The use of flexible edges 118 allows the cervical collar to distribute pressure peaks over larger areas in order to avoid the formation of pressure ulcers. The flexible edges 118 can also prevent pressure peaks even when the collar is improperly applied.

The flexible edges 118 can be integrally formed with the second component of the anterior portion 100 of the orthopedic device, a three-dimensional (3D) anatomically configured proximal support portion 120. The 3D anatomically configured proximal support portion 120 can also be formed as a resilient or flexible overmolded portion. The 3D anatomically configured proximal support portion 120 includes an anatomical, generally cup-shaped portion 122 configured to support, for example, the chin of a wearer.

As best seen in FIGS. 3 and 4, the 3D anatomically configured proximal support portion 120 is formed around and encompasses the supporting spring portion 112.

Orienting indicia 124, such as arrows and/or words indicating the directions that the anterior main support piece 102 is to be applied to the wearer, can be formed directly in the 3D anatomically configured proximal support portion 120 and also on the main support piece 102. It will be recognized that orienting indicia 124 may take any suitable shape or form and can be positioned on any of the components of the orthopedic device.

As best seen in FIG. 4, fold lines 125, 126 are formed in each of the main support piece 102, the flexible edges 118, and the 3D anatomically configured proximal support portion 120. The fold lines 125, 126 may be created, for example, via a living hinge, which is a reduced thickness portion provided between two adjacent portions having a larger thickness. Alternatively, the fold lines 125, 126 may be formed by providing a resilient or compliant interface, such as by overmolding, between the portions that are to be folded over. As shown, the fold lines 125 positioned closer to the center line of the anterior portion 100 may be substantially straight, to allow for a sharp fold, while the fold lines 126 positioned closer to the edges of the anterior portion 100 may be arcuate shaped, to allow for more gradual folds. The fold lines 125, 126 allow the anterior portion 100 to be bent or folded to accommodate different circumferences of anatomical portions. In the exemplary embodiment shown, four fold lines 125 are provided on either side of the access opening 108, however, it will be recognized the more or fewer fold lines may be provided.

In use, the fold lines 125 allow the shape of the anterior portion 100 of the orthopedic device to be such, that when applied to the anatomical portion, the anterior portion 100 has less contact with, and produces less pressure on, the sternomastoid muscle area of the neck and is thus less likely to provide pressure on the veins in the neck. This will in fact decrease the possibility of vascular obstruction of blood which needs to drain from the brain and thus, the cervical collar according to the present disclosure is less likely to increase intracranial pressure.

Figure 12A:
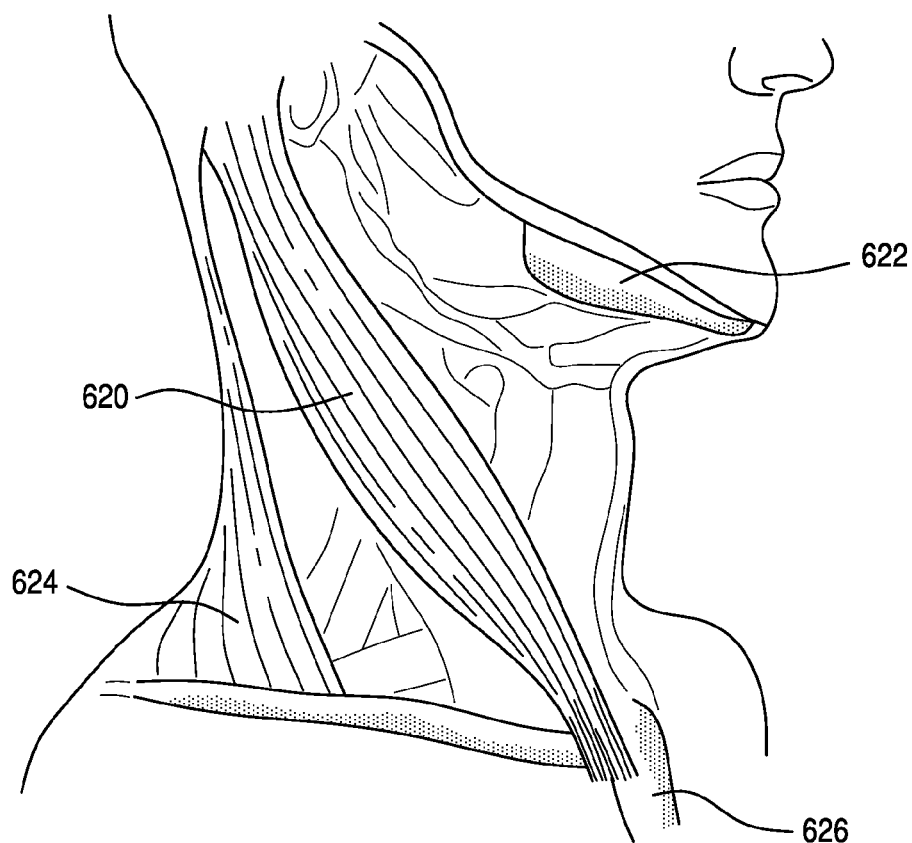
FIG. 12A is a simplified side view of the muscular structure of the neck.
Figure 12B:
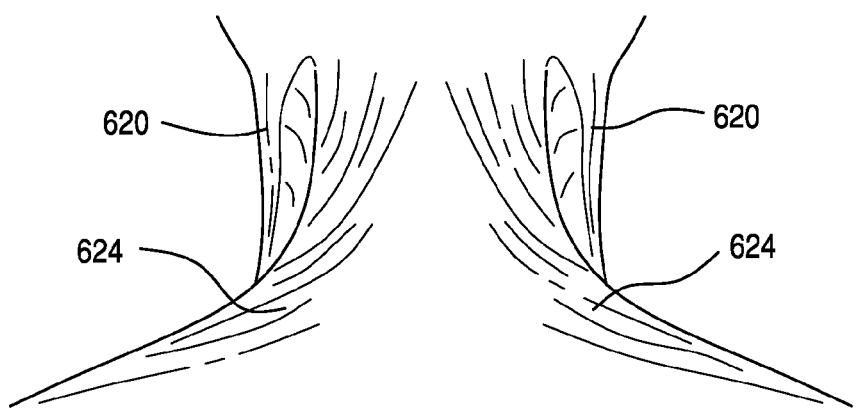
FIG. 12B is a simplified rear view of the muscular structure of the neck.

The generalized structure and musculature of the neck is shown in FIGS. 12A and 12B. As shown in FIG. 12A, the sternocleidomasteoidus (sternomastoid) muscle 620 extends upwardly and posteriorly from the clavicle and sternum 262 toward the mastoid process. The mandible 622 extends anteriorily away from the neck, above the sternomastoid muscle 620. The trapezius muscle 624 wraps around from the back to a position underneath the sternomastoid muscle 620, as shown in FIGS. 12A and 12B.

Figure 14:
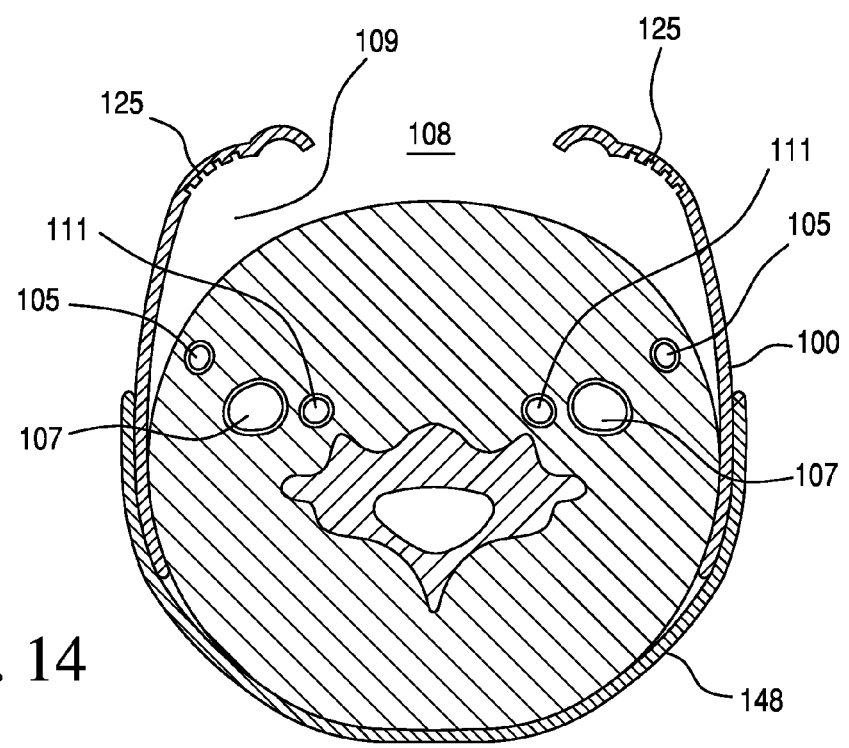
FIG. 14 is a simplified cross-sectional view of the anterior and posterior portions of the cervical collar together in use on a patient and showing the gap formed at the sternomastoid muscle area of the neck so as to be less likely to form pressure on the veins along the neck.

As generally shown in FIG. 14, the carotid artery 111 is positioned within the neck, and supplies blood to the brain. The external 105 and internal 107 jugular veins of the neck drain blood from the brain. The external 105 and internal 107 jugular veins lie relatively close to the surface of the skin, and are thus more susceptible to compression when an external force is applied to the neck, such as, for example, by a rigid cervical collar. Accordingly, the orthopedic device according to this disclosure provides a structure for a cervical collar that allows a gap to be formed between the cervical collar and the sternomastoid muscle area of the neck.

Figure 13:
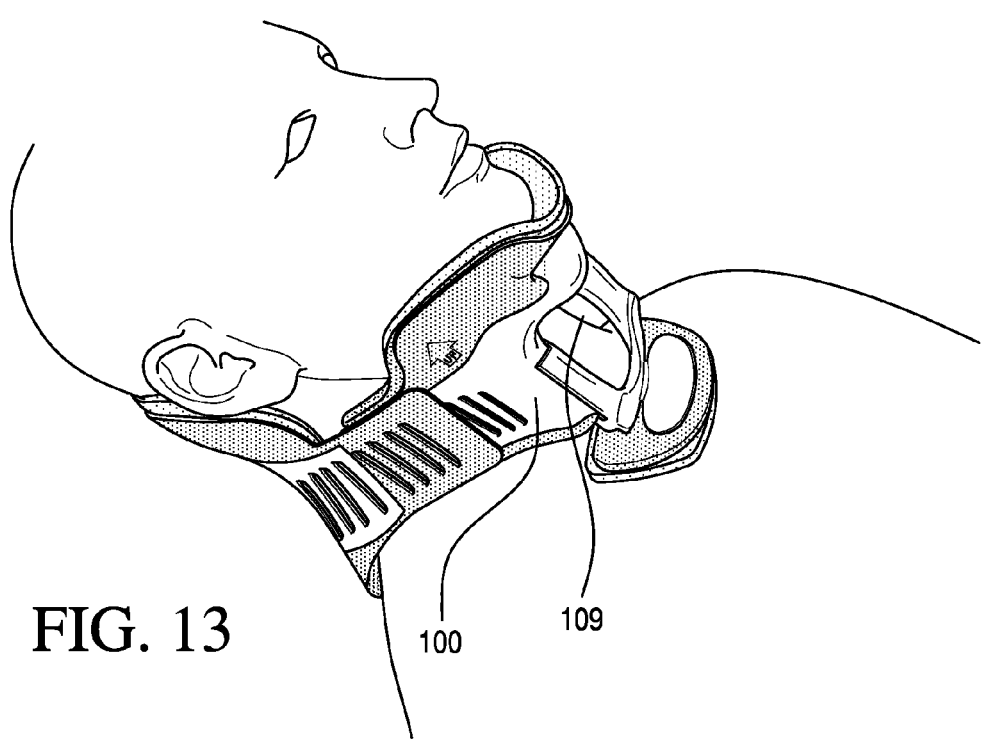
FIG. 13 is a perspective view of the anterior and posterior portions of the cervical collar together in use on a patient exemplifying the clearance or gap between the cervical collar and the sternomastoid muscle area of the neck.

Specifically, the shape of the orthopedic device at the anterior portion 100 thereof, as shown in FIGS. 13 and 14, when applied to the neck of a patient, forms a clearance of the neck veins by way of fold lines 125 in the anterior portion 100 of the collar.

By way of the disclosed structure of the orthopedic device, and as can be seen in FIGS. 13 and 14, pressure applied by the orthopedic device to the body is transferred away from the sternomastoid muscle area of the neck, and in particular, away from the external 105 and internal 107 jugular veins of the neck. The pressure applied by the orthopedic device to the body is instead transferred to other portions of the neck. In particular, the pressure applied by the orthopedic device to the body is transferred to, for example, the trapezius muscle 624, the mandible 622, and the sternum 626.

Figure 10:
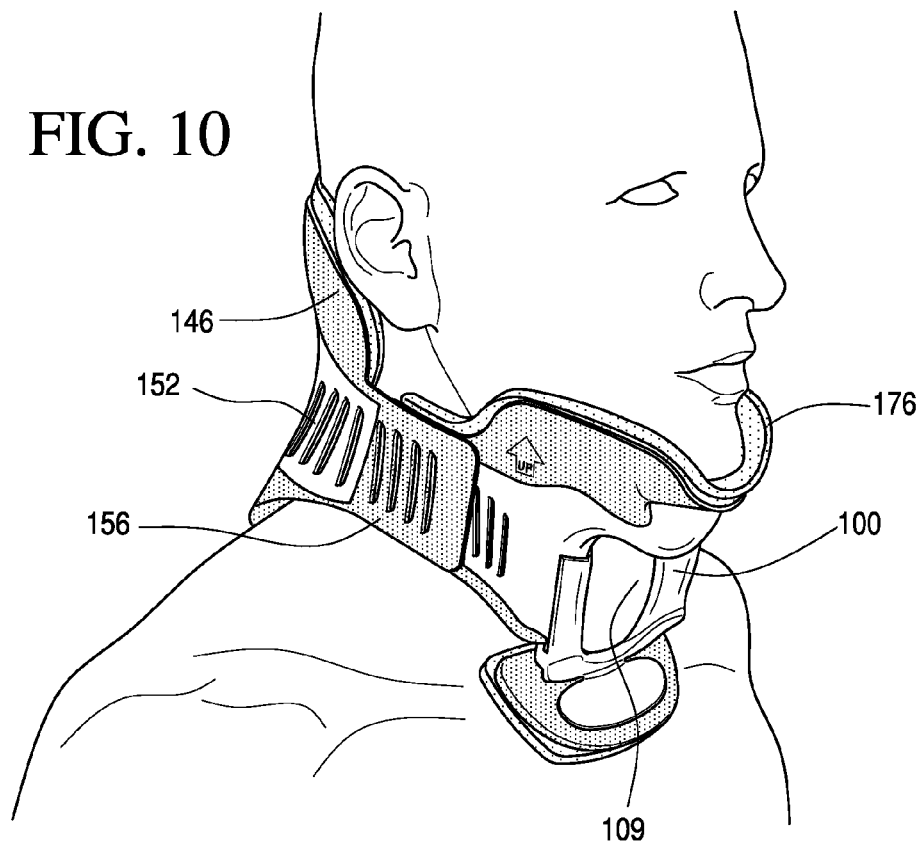
FIGS. 10 and 11 are respectively a front side perspective and rear perspective view of the anterior and posterior portions of the cervical collar together in use on a patient.

In reference to FIGS. 10 and 13, the central portion of the anterior portion 100 of the orthopedic device attaches to the sternal extension adjustment part 130, and is relatively flat, while the curve of the anterior portion 100 of the orthopedic device provided by the fold lines 125 forms a generally rounded corner which defines a gap 109 opposite to the relatively curved surface of the neck at the location of the large cervical veins (vena jugularis externa and interna; external and internal jugular veins) draining blood from the brain, thus, providing reduced vascular obstruction, and reducing the likelihood of an increase in intracranial pressure.

As shown in FIG. 4, the fold lines 125 are provided along a posterior surface of the anterior portion 100 of the orthopedic device. The fold lines 125 are generally arranged perpendicularly on either side of the open access area 108. The fold lines 125 allow the generally rigid or semi-rigid plastic of the orthopedic device to naturally curve into a shape that provides the appropriate clearance for the neck veins, so that there is less vascular obstruction in order to prevent intracranial pressure buildup.

FIG. 14 illustrates the anterior 100 and posterior 148 portions of the cervical collar together in use on a patient as providing a gap 109 formed at the sternomastoid muscle area of the neck so as to be less likely to form pressure on the external 105 and internal 107 jugular veins. As can be seen, the central portion of the anterior portion 100 of the orthopedic device is relatively flat, while the curve of the anterior portion 100 of the orthopedic device provided by the fold lines 125 forms a generally rounded corner which leaves a gap 109 opposite to the relatively curved surface of the neck at the location of the external 105 and internal 107 jugular veins draining blood from the brain, thus, providing reduced vascular obstruction, and reducing the likelihood of an increase in intracranial pressure.

The height of the anterior portion 100 of the orthopedic device can be adjusted to an appropriate size via the use of the third component of the anterior portion 100 of the orthopedic device; the adjustable height support 130. The adjustable height support 130 is configured to be removable from the anterior portion 100, such that the cervical collar can be removed from a patient without removing life support devices that may be connected to the patient in the trachea region, such as breathing and/or feeding tubes. For example, adjustable height support 130 can be removed from the anterior portion 100 of the orthopedic device in order to perform cleaning around or other maintenance of the breathing and/or feeding tubes, while the rest of the orthopedic device remains in place on the patient, or is also removed. Once maintenance is complete, the orthopedic device can be repositioned on the patient and/or the adjustable height support 130 can be reconnected to the orthopedic device.

As best seen in FIG. 3, the adjustable height support 130 includes two upright leg portions 131 configured to cooperate with the depending projections 106. Recessed portions 140 are formed in the upright leg portions 131 and have a corresponding shape to the depending projections 106 for receiving the respective depending projections 106 therein to allow the adjustable height support 130 to be positioned at different heights along the depending projections 106.

As best shown in FIGS. 1, 3, and 4, each upright leg portion 131 includes a locking button 132 that can be manipulated to selectively lock the adjustable height support 130 from being adjusted to a shorter height. The locking buttons 132 are received in appropriately sized and shaped cut out portions of the upright leg portions 131.

As seen in FIGS. 5 and 6, each locking button 132 includes a pivot axle 134, which is received in the upright leg portion 131, to allow the locking button 132 to be pivoted thereon from an engaged, locked position, to a disengaged, unlocked position. At least one locking protrusion 138 is formed on each locking button 132. The locking protrusion 138 is configured to selectively engage a corresponding portion of the cut out portions of the upright leg portions 131 to selectively lock the locking button 132 in the engaged, locked position in order to prevent accidental movement of the adjustable height support 130 to a shorter height.

Teeth 136 are formed along a reduced thickness portion of the pivot axle 134 for selective engagement with the locking projections or ratchets 116 formed on the depending projections 106. The teeth 136 are formed similarly, but in opposition to, the locking projections or ratchets 116, such that the teeth 136 include a first edge having a first thickness that tapers out to a linear edged having a second thickness that is larger than the first thickness, wherein the linear edges of the teeth 136 engage with the linear edges of the locking projections or ratchets 116 to selectively lock the adjustable height support 130 from being adjusted to a shorter height.

When the locking buttons 132 are pivoted to the disengaged, unlocked position, the teeth 136 are removed from contacting the locking projections or ratchets 116 formed on the depending projections 106. Thus, the adjustable height support 130 can freely move either up or down to either decrease or increase the height. In this manner, the position of the adjustable height support 130 on the associated depending projections 106 can be altered to accommodate different anatomical sizes of wearers.

When the locking buttons 132 are pivoted to the engaged, locked position, the teeth 136 are in contact with the locking projections or ratchets 116 formed on the depending projections 106, and the engagement of the linear edges of the teeth 136 and the locking projections or ratchets 116 prevents the movement of the adjustable height support 130 in the upward direction in order to prevent the adjustable height support 130 from being adjusted to a shorter height. However, since the teeth 136 are formed on a reduced thickness portion of the pivot axle 134, the adjustable height support 130 can be moved downward to be adjusted to an increased height, since the reduced thickness portion of the pivot axle 134 provides resiliency to the teeth 136 and allows the tapered portions of the teeth 136 to slide over the tapered portions of the locking projections or ratchets 116.

In this manner, the position of the adjustable height support 130 on the associated depending projections 106 can be adjusted to increase the height without manipulating the locking buttons 132. This feature is a benefit for quickly applying the cervical collar to a patient. The cervical collar can be packaged with the adjustable height support 130 positioned in the shortest height configuration, in order to save on packaging space, and the locking buttons 132 positioned in the engaged, locked position. The cervical collar can be taken directly from the packaging, and the position of the adjustable height support 130 can be increased to accommodate different sized anatomies, simply by pulling downward on the adjustable height support 130.

Fine tuning of the height of the cervical collar can be achieved by pivoting the locking buttons 132 to the disengaged, unlocked position, and adjusting the height of the adjustable height support 130 as needed.

In a variation, the adjustable height support 130 can be replaced with a support that is still removable, but which is not height adjustable. In particular, the support may still have the locking buttons 132, which may engage one set of projections or ratchets 116 formed on the depending projections 106, which projections or ratchets 116 define a single size setting. In this manner, a collar having a specific set height can be provided, while still allowing the collar to be removed from a patient without removing life support.

As shown in FIGS. 1, 3, and 4 the adjustable height support 130 includes a flared distal end that is configured to engage an anatomical portion, such as the sternum, to provide stabilization and support of the main support piece 102 and the 3D anatomically configured proximal support portion 120 with respect to the respective anatomical portions supported thereby, for example, the neck, chin, and jaw.

A hinged distal connecting portion 142 is connected to the distal end of the adjustable height support 130, and includes a footpad 144 thereon. The hinge of the distal connecting portion 142 can be formed as a living hinge, and allows the distal end of the adjustable height support 130 to pivot to accommodate different sizes and shapes of anatomical portions of patients, for example, the sternum. The footpad 144 can be an integrally formed footpad, or a removable and/or replaceable footpad configured to engage an anatomical portion, such as the sternum. To provide comfort to the wearer and to avoid skin ulceration, the footpad 144 can be a resilient or compliant pad formed, for example, by overmolding. The footpad 144 can also be formed as open or closed cell foam padding, and/or, for example, a disposable hydrophilic foam pad.

The anterior portion 100 of the orthopedic device is configured to cooperate with a posterior portion 146 of the orthopedic device to stabilize and support an anatomical portion of a user, as discussed in detail below.

C. Detailed Description of a Posterior Portion of an Orthopedic Device

Figure 8:
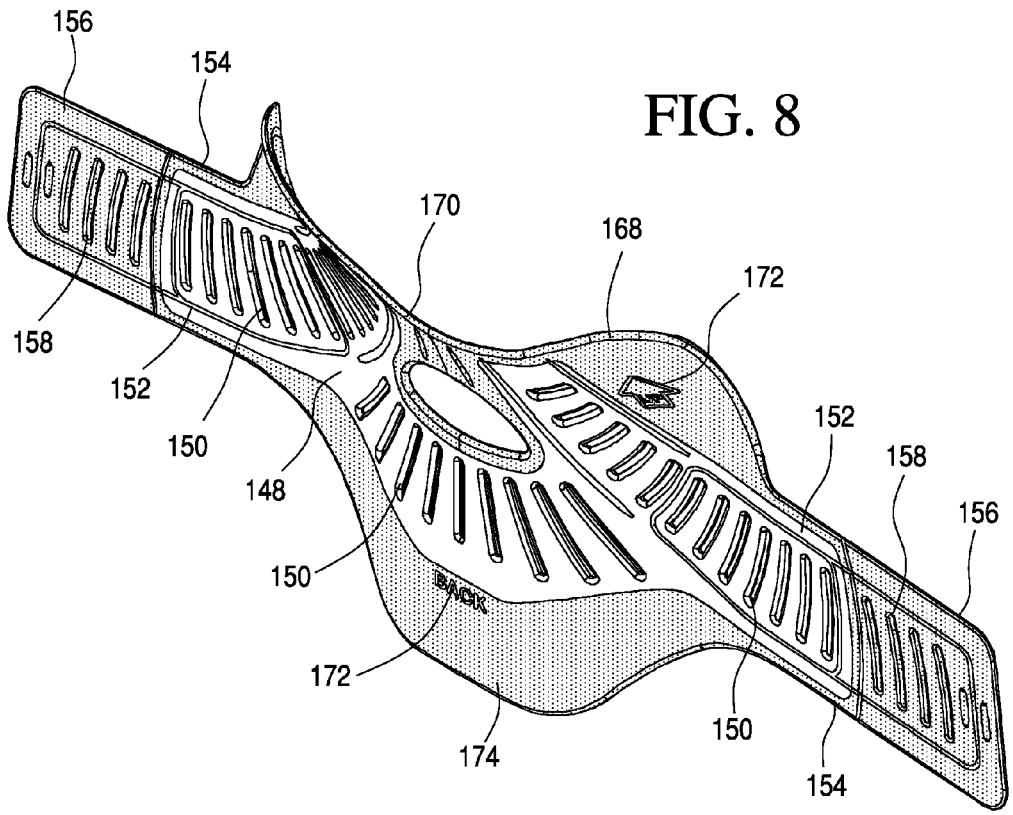
FIG. 8 is a perspective view of the posterior portion of the cervical collar shown in FIG. 7.
Figure 9:
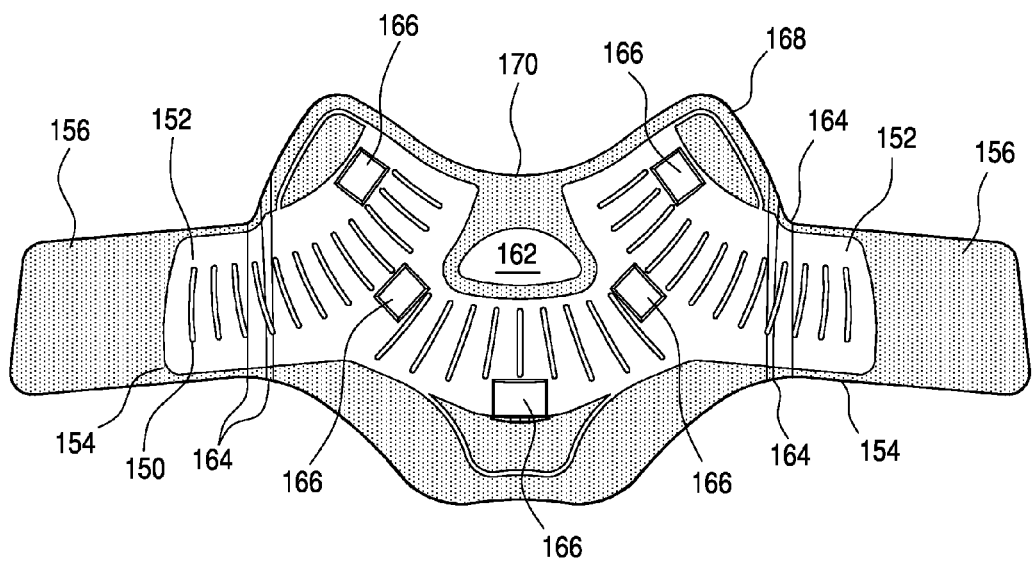
FIG. 9 is a rear view of the posterior portion of the cervical collar shown in FIG. 7.

A posterior portion 146 of an orthopedic device is shown in FIGS. 7-9. The posterior portion 146 of the orthopedic device is constructed in a similar manner as discussed above with respect to the anterior portion, and includes a main support piece 148 and anatomically configured 3D proximal and distal support portions 168, 174.

In a similar manner as previously discussed, the posterior main support piece 148 includes slots 150 that provide ventilation and compliance to the main support piece 148. The slots 150 are formed in three sections of the main support piece 148, the middle section and two upper side sections. The slots 150 in the middle section progress from substantially straight shapes near the center line to slightly arcuate shapes near the edges. The slots 150 in the upper side sections are generally arcuate shapes. The shapes of the slots 150 are specifically configured to provide compliance to the main support piece 148 to allow the posterior portion 146 to conform to different sized anatomical portions of patients. An open cervical access area, 162 is positioned above the middle section and between the upper side sections to provide access to the spine. Further, the main support piece 148 is configured to provide a clearance of the device for the C7 vertebrae.

As with the previously described anterior main support piece, flexible or resilient edges 154 are provided around the periphery of the main support piece 146. The flexible or resilient edges 154 are increased in size from a small flexible edge along the side extending portions 152 that is substantially smaller than the side extending portions 152 to an anatomically configured 3D proximal and distal support portions 168, 174 that may be contiguously formed with the flexible or resilient edges 154 in the proximal and distal central sections. The anatomically configured 3D proximal and distal support portions 168, 174 are of a similar size to the middle section and two upper side sections of the main support piece 148. In this manner, the larger size anatomically configured 3D proximal and distal support portions 168, 174 are able to conform to a large variety of different sizes and shapes of anatomical portions of different users. The flexible or resilient edges 154 and the anatomically configured 3D proximal and distal support portions 168, 174 can be formed, for example, by overmolding.

As best seen in FIG. 8, the proximal support portion 168 includes an anatomically shaped flared section 170 that is shaped to correspond to and support an anatomical portion of a wearer, for example, the occipital region.

As with the anterior portion described above, as shown in FIGS. 8 and 9, orienting indicia 172 are provided on the anatomically configured 3D proximal and distal support portions 168, 174 to indicate the appropriate positioning of the posterior portion 146 of the orthopedic device on the patient. The indicia 172 can be graphically symbolic, and/or alphanumeric in nature, and can be provided in any suitable position on the posterior portion 146.

As best seen in FIG. 9, the anterior surface portion of the posterior portion 146 includes a plurality of liner connection points 166, formed in the same manner and for the same purposes as previously discussed with respect to liner connection points 128. Additionally, fold lines 164, of the same configuration as previously discussed, are also provided to allow the posterior portion 146 of the orthopedic device to be conformed to different sizes and shapes of anatomical portions of patients.

In a slight variation from the anterior portion discussed above, the posterior main support piece 146 includes side extending portions 152 that extend from each side and further include strap portions 156 extending therefrom to aid with circumferential adjustment of the orthopedic device.

The strap portions 156 are formed generally integrally with the flexible or resilient edges 154, and are also flexible or resilient. The strap portions 156 are connected to the side extending portions 152 at trim lines 160, which can be used to more easily remove the strap portions 156 so that the orthopedic device can be used with a proper fit on persons having a very thin anatomical portion, such as a very thin neck.

As can be seen in FIGS. 7 and 8, reduced thickness slots 158 are provided in the strap portions 156. The reduced thickness slots 158 do not pass all the way through the strap portions 156, but still provide additional compliance to allow the strap portions 156 to be more easily bent.

D. Use of Anterior and Posterior Portions Together

Figure 11:
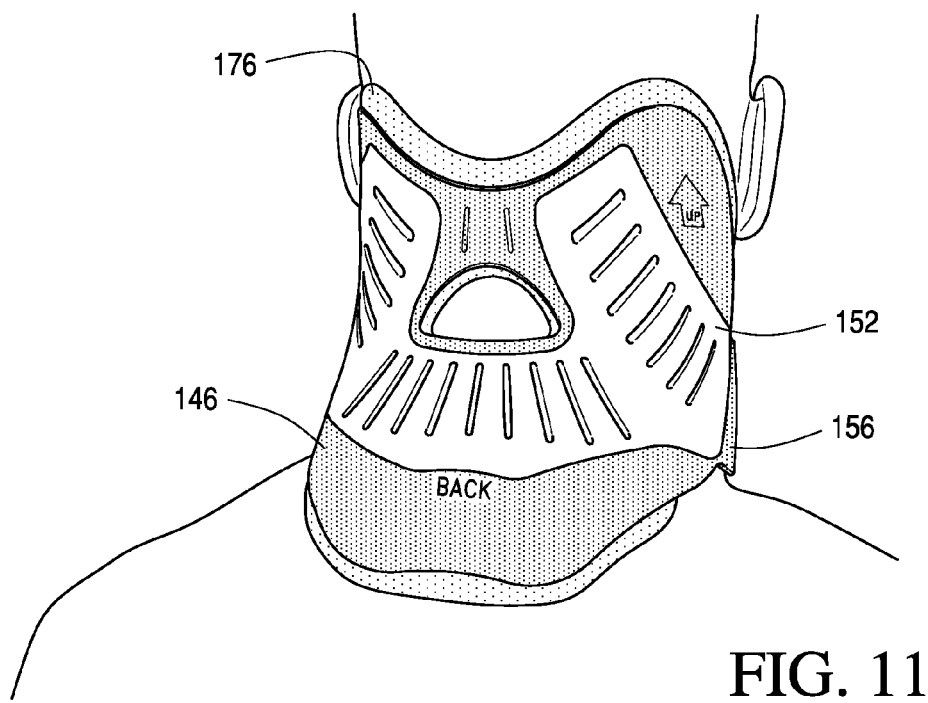

As shown in FIGS. 10, 11, and 13, the anterior and posterior portions 100, 146 are used together to immobilize and stabilize an anatomical portion of a user, such as the neck or cervical area. A two part liner 176 can be provided as an interface between the patient and the respective anterior and posterior portions 100, 146.

As best seen in FIG. 10, the anterior portion 100 is first applied and conformed to the anatomy of the patient. The anterior surface portion of the anterior portion 100 can include integrally formed hooks or loops to form a first part of a hook and loop fastening system. Alternatively, the hooks or loops can be provided as separate pieces that are adhered to the anterior portion 100.

Once the anterior portion 100 is placed on the patient, the posterior portion 146 can be applied. The side extending portions 152 and the strap portions 156 are then folded over the folded portions of the anterior portion 100. Corresponding loops or hooks are similarly integrally formed with or connected to the strap portions 156 (and may be provided on the side extending portions 152 also) for selective engagement with the hooks or loops provided on the anterior portion 100. Since the respective hook and loop fastening elements are provided along a majority of the surfaces of the anterior and posterior portions 100, 146, a wide range of circumferences of anatomical portions of patients can be accommodated.

By way of this strap configuration, there is little to no relative vertical movement between the anterior portion 100 and the posterior portion 146. Thus, the orthopedic device as described herein provides additional immobilization for flexion and extension of the anatomical portion (the neck).

E. Variation of an Orthopedic Device

Figure 15:
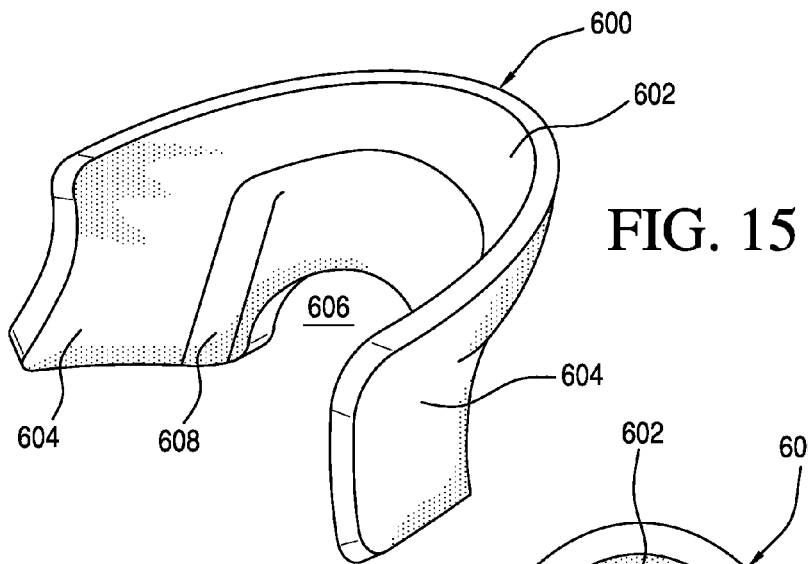
FIG. 15 is a perspective view of an anterior portion of a variation of a cervical collar having reduced vascular obstruction.
Figure 16:
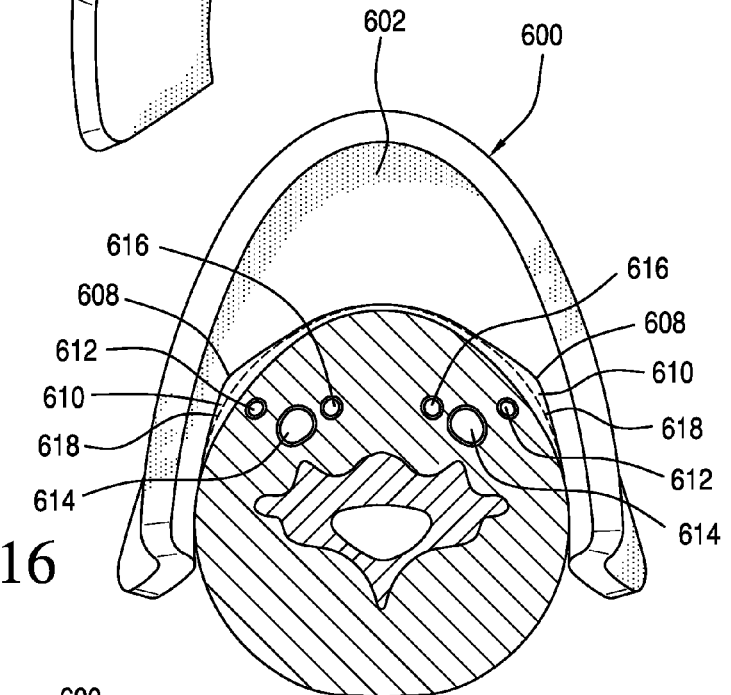
FIG. 16 is a top view of the anterior portion of the cervical collar as shown in FIG. 15, and also generally showing a cross-section of the neck.
Figure 17:
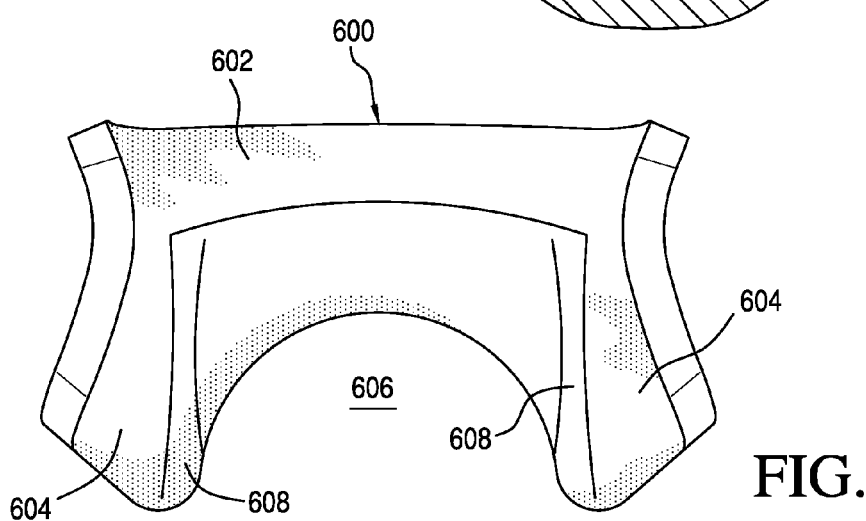
FIG. 17 is a rear view of the anterior portion of the cervical collar as shown in FIG. 15.

A variation of a main support piece of an anterior portion 600 of an orthopedic device is shown in FIGS. 15-17.

While only the anterior portion 600 of the orthopedic device is shown, it will be recognized that a posterior portion of the orthopedic device having a generally similar construction to the anterior portion 600 of the orthopedic device is provided in combination with the anterior portion 600, along with suitable connection mechanisms, such as straps having hook and loop fasteners, to encircle the neck of a patient to provide stabilization and support thereto in a manner that is generally known.

As seen in FIGS. 15 and 16, the anterior portion 600 of the orthopedic device has a generally semi-circular structure for partially surrounding and enclosing an anatomical portion of a patient, for example, the neck. A chin supporting structure 602 extends generally outwardly away from the main support piece of the anterior portion 600 of the orthopedic device.

As best shown in FIGS. 15 and 17, depending projections 604 are formed on each side of the anterior portion 600 of the orthopedic device, and define an open access area 606 therebetween, for example, to provide access to the trachea.

The anterior portion 600 of the orthopedic device can be constructed from a foam material, such as, for example, a closed cell polyethylene foam, for example Plastazote®, which can be water jet cut, C-N-C routed, thermoformed, or pressure-formed. Of course, it will be recognized that any suitable material may be used.

The anterior portion 600 of the orthopedic device can thus be formed as a semi-rigid foam cervical collar portion. As previously discussed, a rigid or semi-rigid cervical collar can produce pressure on the external and internal jugular veins, which may lead to an increase in intracranial pressure.

As best seen in FIG. 16, the anterior portion 600 of the orthopedic device includes recessed surfaces 608 formed on the posterior side of the depending projections 604 of the anterior portion 600 of the orthopedic device. The recessed surfaces 608 are formed so as to provide a gap 610 between the anterior portion 600 of the orthopedic device and the neck, thus providing clearance with, and producing less pressure on, the sternomastoid muscle area of the neck so as to be less likely to form pressure on the external 612 and internal 614 jugular veins in the neck, shown in relation to the carotid arteries 616 in FIG. 16.

Again, with reference to FIG. 16, the posterior surface of the anterior portion 600 of the orthopedic device has an overall generally semi-circular arc 618, shown in dashed line. However, the recessed surfaces 608 are recessed, or bowed, away from the arc 618 so as to be spaced from the sternomastoid muscle area of the neck in order to provide the gap 610. In this manner, the anterior portion 600 of the orthopedic device has a reduced chance of compressing the external 612 and internal 614 jugular veins in the neck, and thus, there is a reduced chance for the buildup of intracranial pressure.

F. Conclusion

It is understood that while the disclosed embodiments are designed to accommodate users having different sized anatomies, the size of the disclosed embodiments and the components thereof can be adjusted so that different users having different sized anatomical portions may benefit from the present designs.

It is understood that while the disclosed embodiments of the orthopedic device are shown having discrete anterior and posterior portions, the anterior and posterior portions may be connected with each other along one side thereof, and a single strap or circumferential adjustment mechanism can be provided between the anterior and posterior portions along the other side thereof.

It will also be recognized that the overmolded edges and 3D anatomical portions, as well as the fold lines, living hinge, and/or slot structures, can be provided to a collar, without providing other features, such as the height adjustability, to the collar.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features from different embodiments. In addition to the variations described herein, other known equivalents for each feature can be mixed and matched by one of ordinary skill in this art to construct an orthopedic device in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A cervical collar, comprising:
   an anterior portion;
   a posterior portion having side extending portions removably connecting to the anterior portion, the posterior portion including a rigid or semi-rigid main support piece and a resilient edge integrally secured to at least a substantial portion of a periphery of the main support piece that is substantially more flexible than the main support piece;
   wherein the resilient edge increases in size from a portion located along the side extending portions and to anatomically configured 3D proximal and distal support portions, the resilient edge being formed contiguously with the main support piece at proximal and distal central regions of the posterior portion.

2. The cervical collar according to claim 1, wherein the anatomically configured 3D proximal and distal support portions are of a similar size and shape to the central region and two proximal side regions of the main support piece.

3. The cervical collar according to claim 1, wherein the anatomically configured 3D proximal and distal support portions conform and support different sizes and shapes of anatomical portions of different users.

4. The cervical collar according to claim 1, wherein the resilient edge is formed along the anatomically configured 3D proximal and distal support portions as a molding located over the main support piece.

5. The cervical collar according to claim 1, wherein the main support piece defines opposed upper side sections extending upwardly toward a proximal middle region, the opposed upper side sections being spaced apart by a distance.

6. The cervical collar according to claim 5, wherein the resilient edge extends between the opposed upper side sections of the main support piece at the proximal middle region.

7. The cervical collar according to claim 5, wherein the posterior portion defines a cervical access opening positioned at a central middle region and below the upper side sections to provide access to a spine of a wearer of the collar.

8. The cervical collar according to claim 1, wherein portions of the main support piece are covered by the resilient edge molded along at least one surface thereof.

9. The cervical collar according to claim 8, wherein at least a segment of the periphery of the main support piece is exposed between portions of the resilient edge located on adjacent sides of the segment.

10. A cervical collar, comprising:
    an anterior portion;
    a posterior portion having side extending portions removably connecting to the anterior portion, the posterior portion including a rigid or semi-rigid main support piece and a resilient edge integrally secured to at least a substantial portion of a periphery of the main support piece that is substantially more flexible than the main support piece;
    flexible strap portions integrally secured with and extending from the side extending portions, the side extending portions formed from at least part from the main support piece and the strap portions formed from the resilient edge;
    wherein the strap portions removably secure to an outer surface of the anterior portions;
    wherein the strap portions extend beyond from elongate trim lines formed adjacent the main support piece.

11. The cervical collar according to claim 10, wherein strap portions define reduced thickness slots that do not pass all the way through the strap portions.

12. A cervical collar, comprising:
    an anterior portion;
    a posterior portion having side extending portions removably connecting to the anterior portion, the posterior portion including a rigid or semi-rigid main support piece and a resilient edge integrally secured to at least a substantial portion of a periphery of the main support piece that is substantially more flexible than the main support piece;
    wherein the proximal support portion defines anatomically shaped flared sections spaced apart by a concave and arcuate section of the resilient edge and shaped to correspond to and support an occipital region of a wearer of the collar.

13. A cervical collar, comprising:
    an anterior portion;
    a posterior portion having side extending portions removably connecting to the anterior portion, the posterior portion including a rigid or semi-rigid main support piece and a resilient edge integrally secured to at least a substantial portion of a periphery of the main support piece that is substantially more flexible than the main support piece;
    wherein an inner surface of the main support piece has less area covered by the resilient edge than an outer surface of the main support piece.

* * * * *